United States Patent [19]

Schönmann et al.

[11] Patent Number: 4,894,978

[45] Date of Patent: Jan. 23, 1990

[54] APPARATUS FOR PREPARING FORMED OR MOLDED BODY

[75] Inventors: Holger Schönmann; Hans P. Eck, both of Eberbach/Baden, Fed. Rep. of Germany

[73] Assignee: R. P. Scherer GmbH, Eberbach/Baden, Fed. Rep. of Germany

[21] Appl. No.: 187,299

[22] Filed: Apr. 28, 1988

Related U.S. Application Data

[63] Continuation-in-part of Ser. No. 285, Jan. 2, 1987, Pat. No. 4,772,472.

[30] Foreign Application Priority Data

Jan. 3, 1986 [DE] Fed. Rep. of Germany ....... 3600084

[51] Int. Cl.[4] .................. B65B 1/04; B65B 47/00
[52] U.S. Cl. ........................ 53/560; 53/238; 53/900; 264/4.3; 424/464
[58] Field of Search .......... 424/464; 427/2, 3; 264/4.3; 514/944; 53/266 R, 267, 268, 900, 238, 560; 425/445, 522, 524

[56] References Cited

U.S. PATENT DOCUMENTS

| | | | |
|---|---|---|---|
| 2,333,433 | 11/1943 | Mabbs | 53/560 |
| 3,032,950 | 5/1962 | Oddo et al. | 53/560 |
| 3,992,854 | 11/1976 | Howell et al. | 53/474 |
| 4,428,927 | 1/1984 | Ebert et al. | 424/440 |
| 4,532,126 | 7/1985 | Ebert et al. | 514/962 |
| 4,567,714 | 2/1986 | Chasman | 53/560 |
| 4,597,885 | 7/1986 | Berry et al. | 252/174.13 |
| 4,609,403 | 9/1916 | Wittwer et al. | 106/136 |
| 4,656,066 | 4/1987 | Wittwer et al. | 106/136 |
| 4,708,834 | 11/1987 | Cohen et al. | 514/966 |

Primary Examiner—Ellis P. Robinson
Assistant Examiner—P. J. Ryan
Attorney, Agent, or Firm—Wells & White

[57] ABSTRACT

A formed or molded body, a manufacturing method and a manufacturing apparatus therefor, wherein several equal or different active ingredients in suitable, equal or different carrier substances are filled at the same time side-by-side without a partition into a uniform enclosure or envelope to provide a formed or molded body with uniform outer appearance and with separate inner regions.

1 Claim, 1 Drawing Sheet

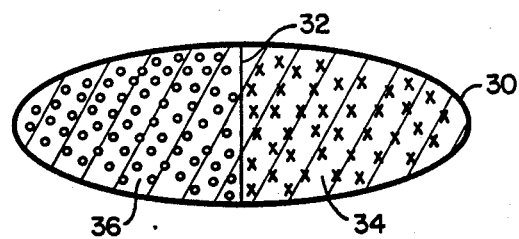
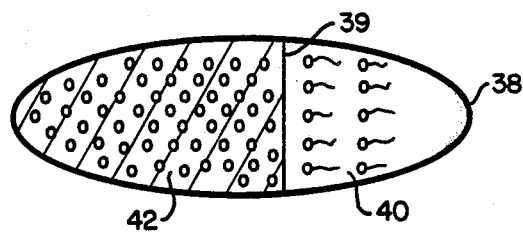
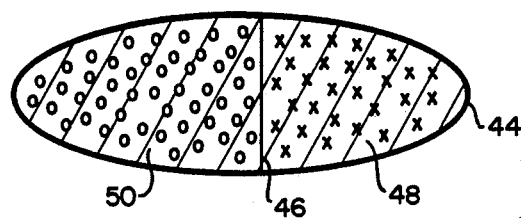
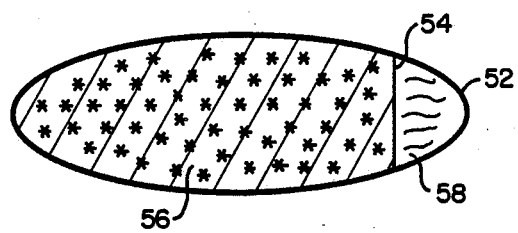
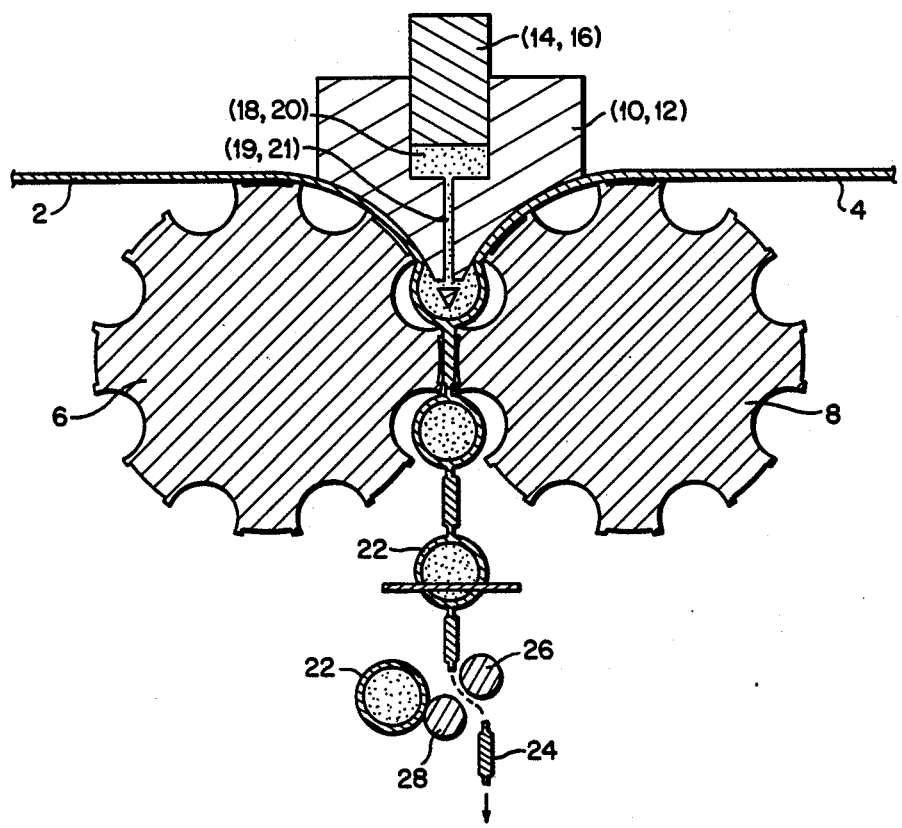

APPARATUS FOR PREPARING FORMED OR MOLDED BODY

CROSS-REFERENCE TO RELATED APPLICATIONS

The present application is a continuation-in-part of application Ser. No. 07/000,285 filed Jan. 2, 1987 now U.S. Pat. No. 4,772,472.

Applicants claim priority under 35 USC 119 for application No. P3600 084.1 filed Jan. 3, 1986 in West Germany.

BACKGROUND OF THE INVENTION

The field of the invention is drug, bio-affecting and body treating compositions and the invention is particularly concerned with capsules.

The present invention relates to a formed or molded body with an enclosure or envelope of polymer material, gelatine or the like, and with a filling in the enclosure or envelope. Generally, the envelope is a hard or soft gelatine capsule that is filled with pharmaceutical preparations. The invention also relates to a method for manufacturing such formed or molded bodies as well as to a corresponding apparatus suitable for manufacturing the molded bodies and for carrying out the method, respectively.

Reference is made to U.S. Pat. Nos. 1,419,618; 2,155,444 and 4,695,466; British Patent No. 2,099,698; West German Patent Publication No. 1,492,077 and Japanese Published Patent application No. 58/206515 as showing the state of the art which is incorporated herein by reference.

For manufacturing soft gelatine capsules the so-called rotary-die-method has substantially been successful. In this method gelatine bands are guided over forming rollers provided with hollow form recesses or dies and the gelatine bands are introduced between these forming rollers. By means of a filling block in the form of a gore or gusset the gelatine bands are pressed into the mold cavities or dies, and on the other hand at the same time the filling substance is injected into the thus formed capsules. Thus, the soft capsules are manufactured and filled in one working step. Thereby, only one uniform substance or a homogeneous substance mixture, i.e., a mixture of several substances, can be filled into the capsules according to this prior art.

Further, hard gelatine capsules are known which are plugged together telescopically from two prefabricated capsule parts. Prior to the plugging together, in a separate working step or steps a uniform substance, a homogeneous mixture of substances or one after the other different layers of substances or substance mixtures are filled into a capsule main body. The manufacturing of such telescoping capsules is, thus, technically more complicated and more expensive than the manufacturing of soft gelatine capsules. In using several different layers of filling substances for hard gelatine capsules, care must be taken that the substances are compatible with each other and that a mixing or mingling of the substances after the filling is permissible.

SUMMARY OF THE INVENTION

Having in mind the limitations of the prior art it is an object of the present invention to provide a formed or molded body, a method of manufacturing and an apparatus therefore wherein a plurality of substances or a mixture of substances defining different phases are filled into one and the same molded body with one operating step so that within the molded body regions of different phases are permanently present.

The active substances can be incompatible with each other or they can react prematurely with each other.

The formed or molded body according to the invention is characterized in that the filling comprises at least two equal active ingredients in two different carrier substances (phases) or at least two different active ingredients in two equal carrier substances (phases), and that the carrier substances (phases) are provided in the enclosure or envelope layered side-by-side without a partition or separating wall.

Accordingly, a method for manufacturing such a formed or molded body according to the invention is characterized in that at least two active ingredients with their associate carrier substances are introduced or filled at the same time into different regions of a common enclosure or envelope and are brought into contact with each other at at least one interface.

Thus, according to the invention a formed or molded body as well as a manufacturing method suitable therefore are provided wherein by simultaneous filling of several substances it is possible to introduce into one single molded body or capsule two or more layered, equal or different phases. Thereby, it is possible on the one hand to accommodate equal active ingredients embedded in different carrier substances or matrices in one and the same envelope as a dose unit in such a manner that for example with pharmaceutical products different resorption velocities can be obtained in the body. On the other hand it is possible to accommodate different active ingredients, which are not compatible with each other or which would intermix with each other in an undesired manner, without a mutual reaction or intermixing by means of equal or different carrier substances or phases side-by-side without partition in a common enclosure or envelope. Thereby the carrier substances or phases form a stable matrix in their associated partial region within the envelope, whereby also a cross-linkage of the carrier substances or a solidification of fillings introduced in a liquid state is possible within the envelope. The carrier substances can also cross-link with the material of the envelope wall, i.e., for example with the gelatine. Principally, equal or similar carrier substances can be used, if it is only secured that an exchange or a reaction or interaction between the active ingredients in the different regions is excluded or a diffusion at the interfaces between the different regions only takes place very slowly or during long time periods.

It is essential for the present invention that at least two equal active ingredients in two different carrier substances or phases are present in the filling, or that at least two different active ingredients in two equal (or different) carrier substances or phases are contained in the filling, whereby the phases are layered side-by-side without a partition or separating wall. However, the two phases at their contact surface form an interface. This interface or contact surface is not necessarily located in the center of the molded body or capsule, i.e., it is not necessary that this interface divides the body into two symmetrical halves, so that the at least two partial volumes may be different in relation to each other. Further, it should be mentioned that the carrier substances for being filled into the body are liquid or at least able to be liquified for injection, whereafter they can become solid. Further, it is important for the filling process that the at least two filling substances (active ingredient plus carrier) are filled or injected into the body or capsule at the same time.

By filling the substances in separate regions of a uniform molded body for example the following advantages can be achieved:

With medicines contained in a gelatine capsule filled with two different, incompatible, medically active substances in at least two equal or different carrier substances there is provided a chemical stabilization of different active ingredients, which are incompatible with each other and which would react on contact with each other, such that they can be stored in one and the same dose unit practically as desired and an interaction of the reactive substances is avoided up to the time at which the molded body is taken by a patient. Only after being taken and after the envelope has been dissolved the active ingredients can then interact with each other.

With a molded body having the features of a gelatine capsule filled with two equal, medically active substances in different carrier substances that are compatible with each other a different resorption of equal or different substances from one and the same molded body can be achieved, whereby for example the active ingredients can become effective in the body of the patient one after the other at the same or different locations.

It is important that the carrier substances (phases) containing the active ingredients are injected by or through at least two conduits or channels at the same time into one common capsule. The word "injection" assumes that there must be a liquid or liquified condition of the carrier substances. By such injection a very precise dosage of the substances and thereby of the active ingredients is achieved.

If after the manufacturing of the filled molded body a certain matrix is formed therein, by the interaction of different matrices the contents of the capsule can still be influenced later to become effective in a retarding manner. Thus, in filling with active ingredients that react in a cross-linking manner with the material of the envelope, for example the gelatine, it is possible to form within a single dose, constituted by the molded body, regions that do not cross-link with each other, so that when the envelope is decomposed, opened or disintegrated within the body of the patient, different partial doses are ensured after a certain time or within a predetermined time period, which partial doses can have special therapeutic effects. Thereby, within one and the same molded body, regions of different solubility can be provided, for instance also in that parts of the envelope are soluble in water or body fluids and other parts of the envelope are scantily soluble or insoluble in the same media, whereby the possibilities of interaction between envelope and/or active ingredient and/or carrier substance are multiplied. Altogether one obtains an improvement in the possibilities for presenting medications whereby physical or chemical incompatibilities of the active ingredients are controlled properly and separately. The active ingredients after filling can also be contained in the common envelope in a manner similar to a sponge and can be released therefrom only slowly.

Examples of the active ingredients include ascorbic acid, thiamine mono nitrate, nicotine amide, calcium-D-pantothenate, riboflavin, cyano-cobalt-balamine, Vitamin B, cloridine hydrochloride, diphene hydramine hydrochloride and extractum radici valerianae sicc.

The carrier substances forming the respective matrix can be lipophil and thus for example can consist of oils, waxes or greases with which the active ingredients are able to be mixed or in which they are soluble. Examples include: bees wax, middle chain tri-glyceride (Miglyol 812 of Dynamit Nobel) and glycerol-tri-fatty acid ester (Softisan 378 of Dynamit Nobel). The carrier substance can also be hydrophil, i.e., formed on the basis of water, as for example poly-glycols and water whereby the active ingredients are mixed, suspended or dissolved in these media. An example of the poly-glycols is polyethylene glycol 400.

The apparatus according to the invention for manufacturing the formed or molded bodies and for carrying out the manufacturing method requires only slight modifications as compared to known capsule manufacturing machines. Substantially, instead of previously one station for supplying the filling medium now a corresponding plurality of such stations is needed. In a manufacturing machine for soft capsules operating according to the so-called "rotary-die-method", thus, two or more supply channels or conduits for the filling medium with a corresponding number of injection nozzles are provided which terminate in one and the same mold cavity that consists of the two form halves of the two forming rollers. Apart from that it is only necessary to redesign the very precisely working supply mechanism such that the filling of different solutions or mixtures is possible in a precise manner also with different viscosities. Thereby not only equal but also different filling substances (equal and/or different active ingredients, equal and/or different carrier substances) can be supplied. Thereby, for example, also components which normally cannot be mixed with each other and which up to now could not be filled in one single working step can now be supplied or introduced into a uniform molded body without a partition in a very precisely dosed manner. According to the state of the art up to now it was only possible to fill premixed homogeneous substances in a dosed manner into a molded body, whereby care had to be taken that the substances did not react with each other during the supply or during the filling or during the storage of the molded bodies. Thus, up to now, it was also not possible to let the active ingredients become effective in the body of a patient one after the other. In many cases a reaction of the different substances occurred already in the store tank or in the supply conduit in front of the filling station so that it was not possible to fill certain substances. By the separate supply and by the separate, however simultaneous introduction or filling into one uniform molded body these problems can be avoided.

BRIEF DESCRIPTION OF THE DRAWINGS

The invention may best be described by reference to the appended drawings, wherein:

FIG. 1 is a plan view in cross-section of a first embodiment of the present invention showing a capsule with two phases where one phase contains calcium pantothenate and the other phase contains ascorbic acid;

FIG. 2 is a plan view in cross-section of a second embodiment of the present invention showing a capsule with two phases where one phase contains clonidin HCl and the other phase contains clonidin HCl in solution;

FIG. 3 is a plan view in cross-section of a third embodiment of the present invention showing a capsule with the two phases where one phase contains extractum Radici Valerianae sicc. and the other phase contains diphenehydramine HCl;

FIG. 4 is a plan view in cross-section of a fourth embodiment of the present invention showing a capsule with two phases where one phase contains an active ingredient in a gel separating matrix and the other phase is a component necessary to form the gel structure; and FIG. 5 is a schematic representation of the apparatus for manufacturing the capsules of the present invention.

DESCRIPTION OF THE PREFERRED EMBODIMENTS

With particular reference to FIG. 5, the apparatus for forming the capsules includes two sheets of warm gelatine material exiting from cooling drums as two endless bands (2, 4) where the gelatine bands are introduced between two rotating forming rollers (6, 8). Filling blocks (10, 12) having dosing pumps (14, 16) are positioned above the forming rollers.

Injection nozzles (19, 21) introduce filling materials simultaneously into a single capsule (22).

The forming rollers at first punch small plates from the gelatine bands and these plates are connected with each other at their edges by the roller pressure. At the same time the dosing pumps (14, 16) press the filling medium (18, 20) through the filling blocks between (into the space between) these two plates, whereby the capsule (22) assumes its final shape.

The capsules (22) are then separated from the scrap gelatine plates (24) by rollers (26, 28).

SPECIFIC EXAMPLES

Example 1

Stable multi-vitamin mixtures

FIG. 1 illustrates the application of Example 1 wherein the capsule 30 has an interface 32 separating formulation 34 from formulation 36. The small circles (o) indicate calcium pantothenate and the small xs (x) indicate ascorbic acid. The diagonal parallel lines (//) represent a fat mixture.

It is known in the art that multi-vitamin mixtures containing the components calcium pantothenate (36) and ascorbic acid (34) are unstable, because these two components (36) and (34) react with each other. Thus, the products made therefrom are not stable over long time periods or they must be provided with great amounts of manufacturing additives, in order to obtain the concentration of the active ingredients of at least 90% required for stability over a long time period. Manufacturing additives of more than 30% are common practice. One possibility to avoid such instability is the coating of component (34) or embedding the mixture in lipophile matrices. Even with this procedure a long time stability cannot be achieved, i.e., also in this case manufacturing additives of the active ingredients of more than 30% are necessary.

According to the present method of separate but simultaneous filling of the components (36) and (34) into one and the same individual body (30) or dose it is possible to obtain a stabilization without additives of active ingredients being necessary. The main point is that the incompatible active ingredients (36) and (34) are contained in one and the same molded body (30) in one and same liquid or liquified matrix at separate locations, so that an interaction will only be possible at the interface (32) between the two parts of the filling. Since the carrier substance or phase will solidify, there is only a negligible interaction of the active ingredients in the area of the interface but not in other areas.

Examples of prior art:

|  | mg per capsule | guaranteed content | % additive |
|---|---|---|---|
| Ascorbic acid | 220.0 | 200.0 | 10 |
| Thiamine mono-nitrate | 11.5 | 10.0 | 15 |
| Nicotine amide | 105.0 | 100.0 | 5 |
| Calcium-D-pantothenate | 35.0 | 20.0 | 75 |
| Riboflavin | 11.0 | 10.0 | 10 |
| Cyano-co-balamine 0.1% | 5.4 | 4.0 mcg Vit. B12 | 35 |
| DL-alpha-Toco-pherol-acetate | 30.6 | 30.0 | 2 |
| Vit. A palmitate with 1 Mio IE Vit. A/g | 6.6 | 6000E | 10 |
| middle chain Tri-glyceride (Miglyol 812)* | 264.9 |  |  |
| Glycerol-tri-fatty-acid ester (Softisan 378)* | 120.0 |  |  |
|  | 810.0 |  |  |

*Manufacturer: Dynamit Nobel, Witten, West-Germany

Example 1 for the present invention:

|  | mg per capsule | guaranteed content | % additive |
|---|---|---|---|
| Formulation 34: |  |  |  |
| Ascorbic acid | 220.0 | 200.0 | 10 |
| Thiamine mono-nitrate | 11.5 | 10.0 | 15 |
| Miglyol 812 | 148.5 |  |  |
| Softisan 378 | 60.0 |  |  |
|  | 440.0 |  |  |
| Formulation 36: |  |  |  |
| Nicotine amide | 105.0 | 100.0 | 5 |
| Calcium-D-pantothenate | 35.0 | 20.0 | 75 |
| Riboflavin | 11.0 | 10.0 | 10 |
| Cyano-co-balamine 0.1% | 5.4 | 4.0 mcg Vit. B12 | 35 |
| DL-alpha-Toco-pherol-acetate | 30.6 | 30.0 |  |
| Vit. A palmitate with 1 Mio IE Vit. A/g | 6.6 |  |  |
| Miglyol 812 | 116.4 |  |  |
| Softisan 378 | 60.0 |  |  |
|  | 370.0 |  |  |
|  | 810.0 |  |  |

Vitamin B1 is the most stable in the acid pH-area and thus, is injected together with the Ascorbic acid by one conduit (19). In contrast, the other vitamins, for example calcium pantothenate, are more stable at higher pH-values and thus are injected into the capsule separately from the ascorbic acid, but simultaneously, by a second conduit (21).

Example 2

Initial and Retarded Dosage

FIG. 2 illustrates the application of Example 2 wherein the capsule 38 has an interface 39 separating formulation 40 from formulation 42. The small circles (o) indicate clonidine HCl and the small circles with a tail indicate clonidine in solution. The diagonal parallel lines (//) indicate a fat mixture and the parallel wavy lines ($\approx$) indicate poly-ethylene-glycol 400.

With many active ingredients it is desirable to work with an initial dosage and with another time-delayed dosage maintaining the effect. This can for example be achieved by coating a part of the active material with a, for example, pH-dependent lacquer or varnish. In this manner there is achieved in the stomach of the patient an initial resorption, i.e., an initial effect, and thereafter, depending on the further transport of the active ingredient, a further resorption of the material protected by the lacquer or varnish. Another possibility consists in obtaining a different, time-delayed resorption by variation of the grain size or the crystal structure.

The present invention now describes as Example 2 a further possibility of obtaining such a product. By using different polar phases the same active ingredient (the same active combination) is filled into the different areas in one working step.

By the different polarity of the phases it does not matter whether the molded body later on maintains this exact separation in space or not. It is only essential that other methods, as for example emulgating, do not ensure that in the individual molded body a precise dosage of the active ingredients is present. Thus, in the present application it is pointed out that not only the substances are filled in separately, but simultaneously, but also they can be and are dosed or metered very precisely.

Example 2 for the present invention:

| Formulation 40: | |
|---|---|
| Clonidine hydrochloride | 0.1 mg |
| Poly-ethylene-glycol 400 | 99.9 mg |
| | 100.0 mg |
| Formulation 42: | |
| Clonidine hydrochloride | 0.15 mg |
| bees wax | 10.00 mg |
| vegetable oil | 89.35 mg |
| Lecithin | 0.50 mg |
| | 100.00 mg |

A first part of the clonidine hydrochloride is dissolved in poly-ethylene-glycol 400 and injected into the capsule by one conduit (19). The second part of the clonidine hydrochloride is suspended in a melt of bees wax and vegetable oil by addition of Lecithin, and this formulation is injected into the capsule at the same time by a second conduit (21). The poly-ethylene-glycol solution is the initial dose, and the suspension in bees wax and vegetable oil will effect the retarding function in vivo.

Example 3

Filling of an extract mixture in which one component reacts in an interlacing manner with the gelatine envelope, i.e., the latter becomes insoluble FIG. 3 illustrates the application of Example 3 wherein the capsule 44 has an interface 46 separating soluble material 48 from insoluble material 50. The small circles (o) indicate extractum Radici Valerianae sicc. and the small xs (x) indicate diphene hydramine HCl. The diagonal parallel lines (//) represent a fat mixture.

In many active ingredients originating from natural sources the tanning (interlacing) effect is a disadvantage, limiting or preventing the use of gelatine as an envelope for the individual dose. By the simultaneous but separate filling of the individual dose, however, it becomes possible to arrange the tanning or interlacing active ingredients in the individual dose such that the entire body still satisfies the regulations of medicinal law, i.e., the release of the active ingredient from the individual body is ensured with sufficient certainty.

Example 3: Tanning active ingredients

| Formulation 50: | |
|---|---|
| Extractum Radici Valerianae sicc. | 50.0 mg |
| Miglyol 812 | 60.0 mg |
| Softisan 378 | 30.0 mg |
| | 140.0 mg |
| Formulation 48: | |
| Diphene hydramine hydrochloride | 25.0 mg |
| Miglyol 812 | 35.0 mg |
| Softisan 378 | 20.0 mg |
| | 80.0 mg |

Formulations 48 and 50 are injected at the same time by means of separate conduits (19, 21) into the capsule. That area of the capsule envelope contacting the valerian extract after a certain time becomes insoluble. That area of the capsule envelope contacting the non-interlacing diphene hydramine hydrochloride remains (at least theoretically) soluble, so that the capsule will be dissolved in this area when it is examined according to the medicinal law.

Example 4

Manufacturing of a filling material forming a definite structure, filled into individual doses FIG. 4 illustrates the application of Example 4 wherein the capsule 52 has an interface 54 separating an active ingredient 56 from a component 58 necessary for gel structure. The stars (*) indicate the active ingredient and the wavy lines ($\approx$) indicate the component necessary for a gel structure. The diagonal parallel lines (//) represent a gel separating matrix.

Many components of filling materials react with each other by forming a structure which may for example be a gel structure. These structures partially are so rigid or tough (highly viscous) that the mixtures can no longer be injected. For this reason it is desirable that the definite desired formation of the structure takes place only after the filling process, i.e., only within the envelope of the body in the individual dose.

The difficulty now is to produce an exact amount of an individual dose of such a mixture without running the risk that the filling process will be made more difficult or even impossible by the formation of the structure that cannot be controlled exactly and which is in addition partially accelerated by catalytic effects. Especially in mass production this is a limitation resulting in the fact that such mixtures have not been produced in the past.

The present invention provides a possibility to fill such materials at the same time at separate locations into one and the same unit, hereby the difficulties in the production technology of such mixtures are avoided and the manufacturing of such products is made possible.

We claim:

1. An apparatus for manufacturing a formed body having a common enclosure of polymer material and a filling inside said enclosure consisting essentially of:
   (a) means for delivering two endless bands of polymer material;
   (b) a plurality of rotating rolls adapted to form said common enclosure from said endless bands; and
   (c) means located above said rotating rolls for delivering said filling material through nozzle means to said common enclosure; the improvement comprising:
(d) said means for delivering said filling material comprising within one single filling block a plurality of parallel conduits and a corresponding plurality of nozzles introducing a plurality of different phases of said filling material simultaneously into said common enclosure.

* * * * *